US012150879B2

(12) United States Patent
Chiang et al.

(10) Patent No.: US 12,150,879 B2
(45) Date of Patent: Nov. 26, 2024

(54) JOINT ORTHOSIS ASSEMBLY

(71) Applicants: Plus Meditech Co., Ltd., Tainan (TW); OPPO MEDICAL INC., Seattle, WA (US)

(72) Inventors: Yueh-Hua Chiang, Taipei (TW); Kuo-Wei Lee, Taipei (TW); Ming-Jhih Wu, Taipei (TW); Rene Winfried Schiller, Taipei (TW)

(73) Assignees: Plus Meditech Co., Ltd., Tainan (TW); OPPO MEDICAL INC., Seattle, WA (US)

( * ) Notice: Subject to any disclaimer, the term of this patent is extended or adjusted under 35 U.S.C. 154(b) by 507 days.

(21) Appl. No.: 16/983,645

(22) Filed: Aug. 3, 2020

(65) Prior Publication Data
US 2021/0315722 A1      Oct. 14, 2021

(30) Foreign Application Priority Data

Apr. 8, 2020   (TW) ................... 109111806

(51) Int. Cl.
*A61F 5/00*     (2006.01)
*A61F 5/01*     (2006.01)

(52) U.S. Cl.
CPC ................... *A61F 5/0125* (2013.01)

(58) Field of Classification Search
CPC .... A61F 5/0104; A61F 5/0106; A61F 5/0109; A61F 5/0123; A61F 5/0125; A61F 5/013; A61F 5/05841; A61F 5/0585; A61F 5/05858; A44B 1/00–44; Y10T 403/32032; Y10T 403/32196; Y10T 403/32311; Y10T 403/32565;
(Continued)

(56) References Cited

U.S. PATENT DOCUMENTS 161,920 A  *  4/1875  Beaumont ............ B26D 1/0006
                                                 83/857
3,817,244 A  *  6/1974  Taylor ................... A61F 5/0123
                                                 602/26
(Continued)

FOREIGN PATENT DOCUMENTS

EP         1462072 A1    9/2004
WO    2010/087899 A2    8/2010

OTHER PUBLICATIONS

Search Report appended to an Office Action, which was issued to Taiwanese counterpart application No. 109111806 by the TIPO on Aug. 25, 2020 (2 pages).

*Primary Examiner* — Adam Baker
(74) *Attorney, Agent, or Firm* — Osha Bergman Watanabe & Burton LLP (57) ABSTRACT

A joint orthosis assembly includes a web, an arm unit, a strap unit, and at least one fastening subassembly. The web has three web portions for being wrapped on an upper limb structure, a lower limb structure, and a joint between the upper and lower limb structures, respectively. The arm unit is retained on the web and includes two arms which are pivotally connected, and which are for being disposed at lateral sides of the upper and lower limb structures, respectively. The strap unit includes two straps each being wound about the web to be coupled between the two arms. The fastening subassembly is configured to permit an end of at least one of the straps to be turnably coupled to a corresponding one of arms.

13 Claims, 11 Drawing Sheets

(58) Field of Classification Search
CPC ..... Y10T 403/32573; Y10T 403/32631; Y10T 403/32672; Y10T 403/32681; Y10T 24/45471; Y10T 24/45492; Y10T 24/45602; Y10T 74/20165; Y10T 29/49853; Y10T 29/53104
See application file for complete search history.

(56) References Cited

U.S. PATENT DOCUMENTS

| | | | | |
|---|---|---|---|---|
| 4,033,012 | A * | 7/1977 | Kramer | A44B 1/28 24/95 |
| 5,626,557 | A * | 5/1997 | Mann | A61F 5/012 602/26 |
| 5,782,780 | A * | 7/1998 | Mason | A61F 5/0123 602/26 |
| 5,873,847 | A * | 2/1999 | Bennett | A61F 5/013 16/342 |
| 7,473,236 | B1 * | 1/2009 | Mathewson | A61F 5/0104 602/26 |
| 8,167,829 | B2 * | 5/2012 | Sterling | A61F 5/0123 602/26 |
| 10,051,923 | B2 | 8/2018 | Omarsson et al. | |
| 2008/0208095 | A1 * | 8/2008 | Kazmierczak | A61F 5/0123 602/26 |
| 2013/0178772 | A1 * | 7/2013 | Oaks | A61F 5/0123 602/26 |
| 2014/0298624 | A1 * | 10/2014 | Omarsson | A44B 11/22 24/265 EC |
| 2017/0348131 | A1 * | 12/2017 | Petursson | A61F 5/0123 |
| 2019/0048923 | A1 * | 2/2019 | Gunnsteinsson | E05D 1/02 |
| 2021/0186734 | A1 * | 6/2021 | Bauerfeind | A61F 5/0109 |

* cited by examiner

JOINT ORTHOSIS ASSEMBLY

CROSS-REFERENCE TO RELATED APPLICATION

This application claims priority from Taiwanese invention patent application no. 109111806, filed on Apr. 8, 2020.

FIELD

The disclosure relates to a joint orthosis assembly, more particularly to a joint orthosis assembly for stabilizing a joint between an upper limb structure and a lower limb structure.

BACKGROUND

An existing knee orthosis usually includes a tubular web, a supporting linkage, and two straps. The tubular web is sleeved on a leg of a patient. The supporting linkage and the straps are positioned on the tubular web around a knee joint of the leg for compressing the outer and inner sides of the leg so as to stabilize the knee joint and to relieve the pain caused by osteoarthritis (OA).

One end of each of the straps is fixed to the tubular web and the other end is folded back through a ring of the supporting linkage so that each of the straps has a tightened segment which is tightened on the tubular web, and a folded-back segment which is fastened to the tightened segment by means of a Velcro fastener.

During ongoing movement of the patient's leg from an extended position to a flexed position, the tubular web and the supporting linkage bend with the leg. Because two ends of each of the straps are not turnably fastened respectively to the tubular web and the support linkage, the strips, during the movement of the leg, may slide on the tubular web and may not be always fittingly tightened on the tubular web. Therefore, the existing knee orthosis may not effectively stabilize the knee joint.

SUMMARY

Therefore, an object of the disclosure is to provide a novel joint orthosis assembly which may overcome at least one drawback of the prior art.

According to the disclosure, a joint orthosis assembly is provided for stabilizing a joint between an upper limb structure and a lower limb structure. The joint orthosis assembly includes a web, an arm unit, a strap unit, and at least one fastening subassembly. The web has an upper web portion for being wrapped on the upper limb structure, a lower web portion for being wrapped on the lower limb structure, and a middle web portion disposed between the upper and lower web portions for being wrapped around the joint. The arm unit includes an upper arm for being disposed at a lateral side of the upper limb structure, and a lower arm for being disposed at a lateral side of the lower limb structure. Each of the upper and lower arms includes a pivot end portion and a coupled end portion which is coupled to be retained on a respective one of the upper and lower web portions. The pivot end portions of the upper and lower arms are pivotally connected to each other on the middle web portion. The strap unit includes a first strap and a second strap which are wound about the web to intersect with each other. Each of the first and second straps is coupled between the coupled end portions of the upper and lower arms. The at least one fastening subassembly is configured to permit an end of at least one of the first and second straps to be turnably coupled to a corresponding one of the coupled end portions of the upper and lower arms.

BRIEF DESCRIPTION OF THE DRAWINGS

Other features and advantages of the disclosure will become apparent in the following detailed description of the embodiment(s) with reference to the accompanying drawings, in which.

DETAILED DESCRIPTION

Before the disclosure is described in greater detail, it should be noted that where considered appropriate, reference numerals have been repeated among the figures to indicate corresponding or analogous elements, which may optionally have similar characteristics.

To aid in describing the disclosure, directional terms may be used in the specification and claims to describe portions of the present disclosure (e.g., front, rear, left, right, top, bottom, etc.). These directional definitions are intended to merely assist in describing and claiming the disclosure and are not intended to limit the disclosure in any way.

Figure 1:
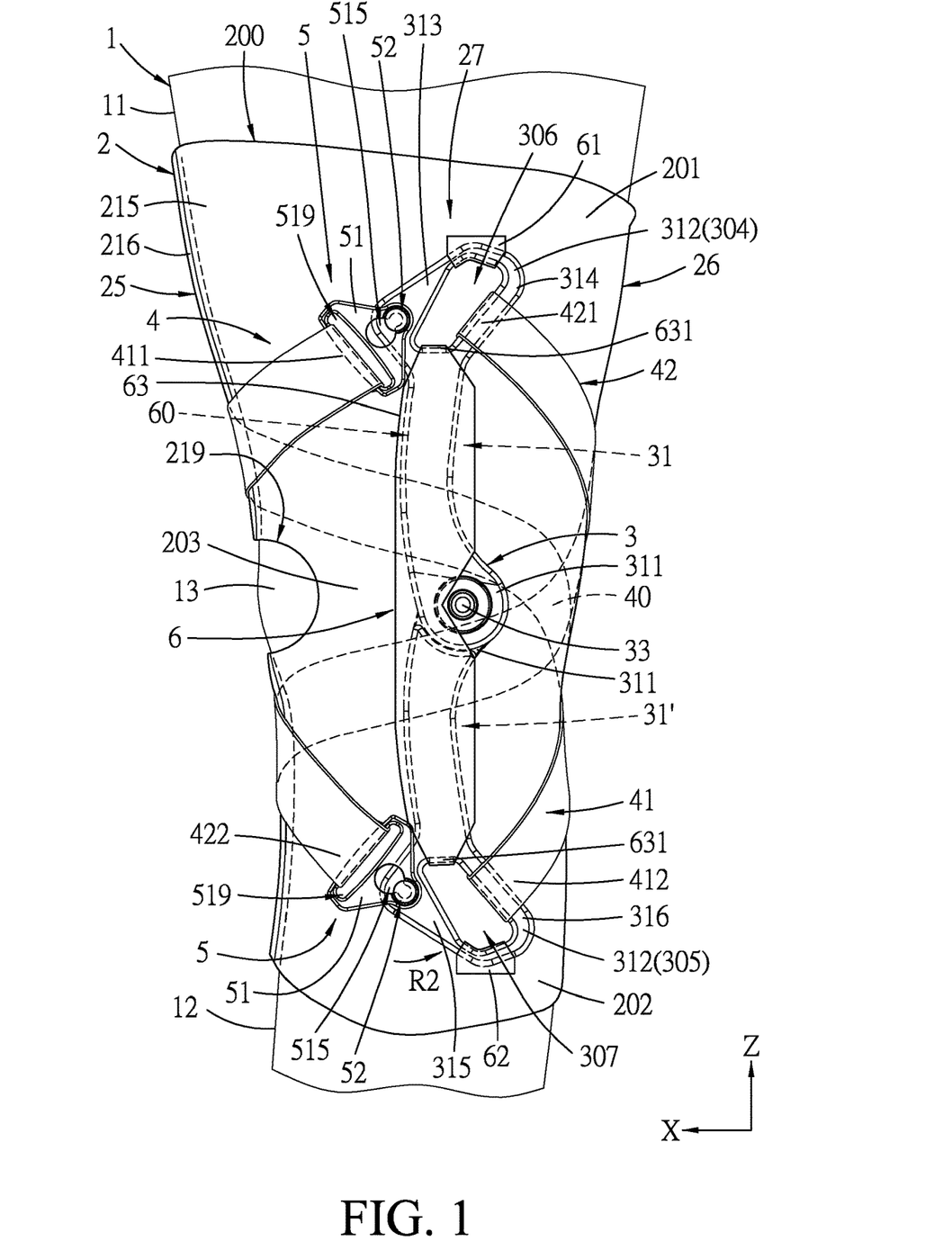
FIG. 1 is a side view of a joint orthosis assembly according to a first embodiment of the disclosure, illustrating a state of the joint orthosis assembly when a leg of a patient is in an extended position.
Figure 2:
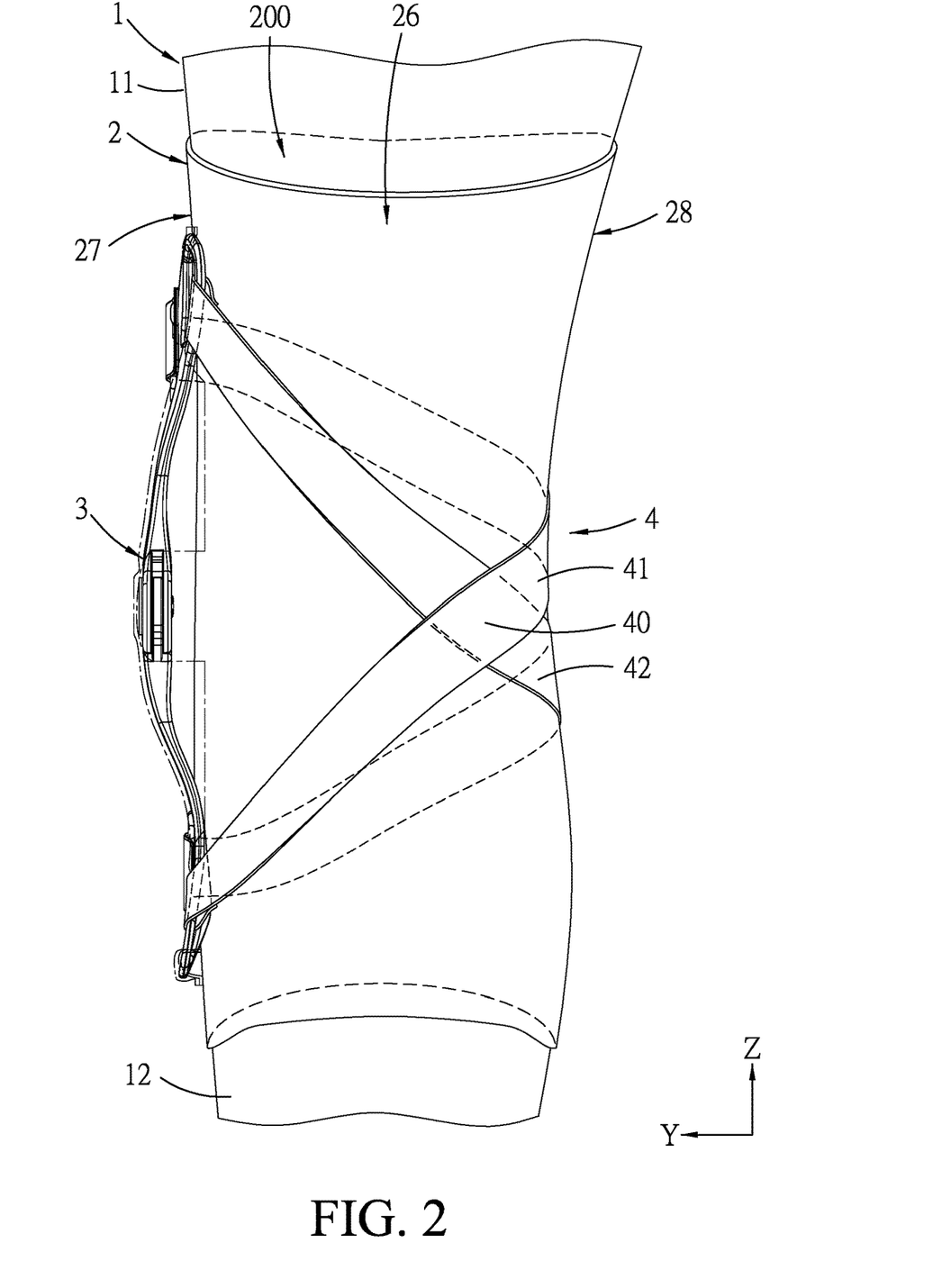
FIG. 2 is a back view of the first embodiment.

Referring to FIGS. 1 and 2, a joint orthosis assembly 200 according to a first embodiment of the disclosure is provided for stabilizing a joint 13 between an upper limb structure 11 and a lower limb structure 12. In an embodiment shown in FIG. 1, the joint orthosis assembly 2 is exemplified but not limited for being worn on a left leg 1 of a patient with osteoarthritis. The upper limb structure 11 is a thigh limb, the lower limb structure 12 is a calf limb, and the joint 13 is a knee joint. By compressing outer and inner sides of the leg 11 using the joint orthosis assembly 200, the knee joint 13 may be stabilized and the pain caused by osteoarthritis may be relieved. In the following, the joint orthosis assembly 2 defines an upright direction (Z), a front-rear direction (X) perpendicular to the upright direction (Z), and a left-right direction (Y) perpendicular to both the upright direction (Z) and the front-rear direction (X).

Figure 3:
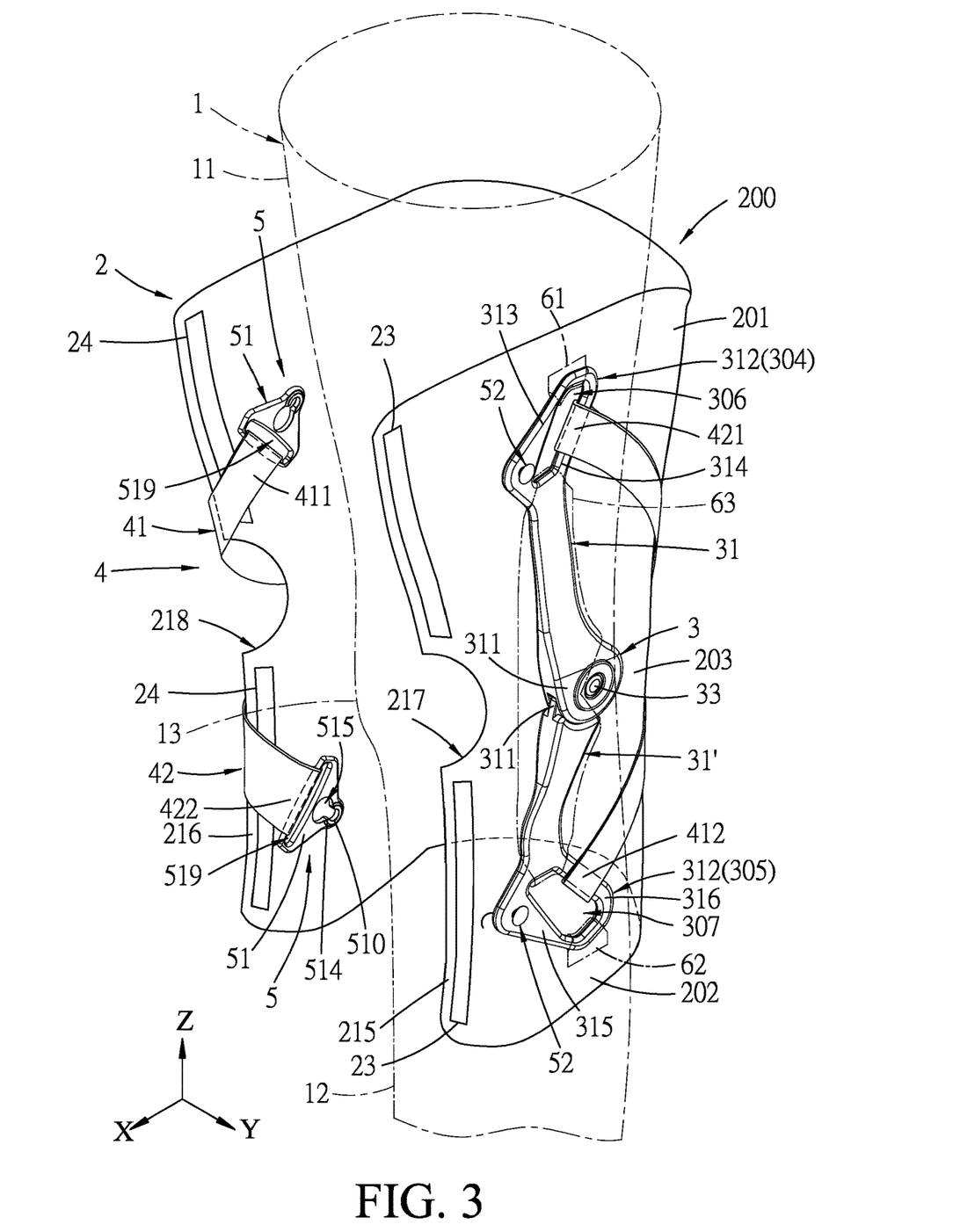
FIG. 3 is a perspective view of the first embodiment illustrating two marginal regions of a web detached from each other.

Referring to FIGS. 1 and 3, the joint orthosis assembly 200 is shown to include a web 2, an arm unit 3, a strap unit 4, and at least one fastening subassembly 5.

The web 2 has an upper web portion 201 for being wrapped on the upper limb structure 11, a lower web portion 202 for being wrapped on the lower limb structure 12, and a middle web portion 203 disposed between the upper and lower web portions 201, 202 for being wrapped around the joint 13.

In an embodiment shown in FIGS. 1 and 3, the web 2 is made of an elastically stretchable material, and extends circumferentially to terminate at a first marginal region 215 and a second marginal region 216 which are configured to be detachably fastened to each other so as to form an opening 219 for exposing an anterior of the joint 13. In this embodiment, a patella of the knee joint 13 is permitted to extend out from the opening 219.

In an embodiment shown in FIG. 3, the first marginal region 215 is provided with, on an outer surface thereof, two first fastening strips 23 located respectively at the upper and lower web portions 201, 202, and has a first semicircular cutout 217 located at the middle web portion 203. The second marginal region 216 is provided with, on an inner surface thereof, two second fastening strips 24 located respectively at the upper and lower web portions 201, 202, and has a second semicircular cutout 218 located at the middle web portion 203. When the first fastening strips 23 are respectively brought into fastening engagement with the second fastening strips 24 to couple the first and second marginal regions 215, 216 together, the web 2 is tightly wrapped on the leg 1 and the first and second semicircular cutouts 217, 218 form the opening 219 which is substantially circular. The first fastening strips 23 may be, for example, stitched to the first marginal region 215, and may have one of hook and loop materials of a Velcro fastener. The second fastening strips 24 may be, for example, stitched to the second marginal region 216, and may have the other one of hook and loop materials of the Velcro fastener, thereby allowing the first and second marginal regions 215, 216 to be detachably fastened to each other.

As shown in FIGS. 1 and 2, when the web 2 is wrapped on the leg 1, the web 2 defines a front side 25, a rear side 26 opposite to the front side 25 in the front-rear direction (X), a first lateral side 27, and a second lateral side 28 opposite to the first lateral side 27 in the left-right direction (Y). In an embodiment, the first lateral side 27 corresponds in position to the outer side of the leg 1, and the second lateral side 28 corresponds in position to the inner side of the leg 1.

Figure 7:
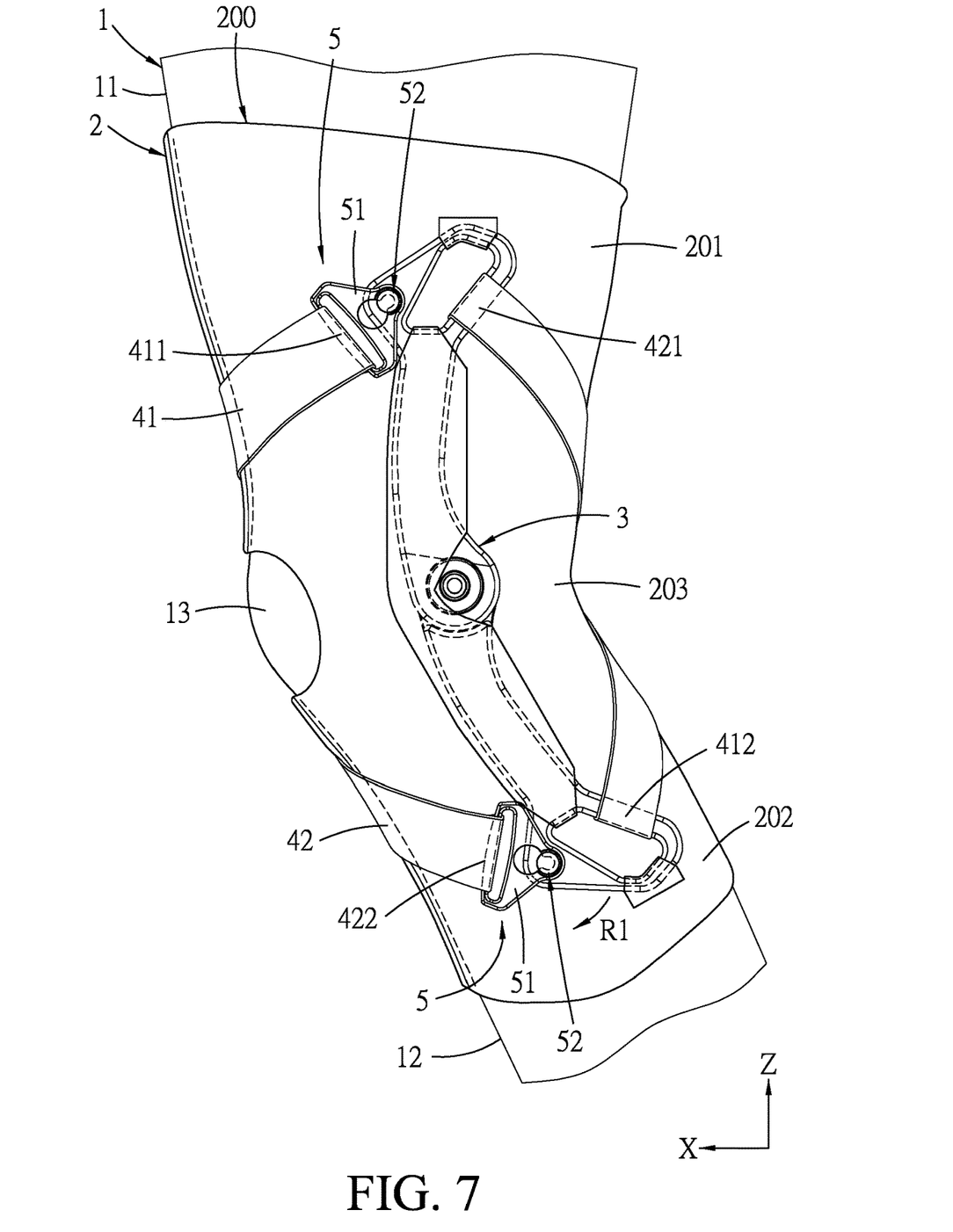
FIG. 7 is similar to FIG. 1 but illustrating a state of the joint orthosis assembly when the patient's leg is in a flexed position.

The arm unit 3 includes an upper arm 31 and a lower arm 31'. The upper arm 31 is disposed at a lateral side of the upper limb structure 11 for providing a support to the upper limb structure 11. The lower arm 31' is disposed at a lateral side of the lower limb structure 12 for providing a support to the lower limb structure 12. Each of the upper and lower arms 31, 31' includes a pivot end portion 311 and a coupled end portion 312 which is coupled to be retained on a respective one of the upper and lower web portions 201, 202. The pivot end portions 311 of the upper and lower arms 31, 31' are pivotally connected to each other on the middle web portion 203 by means of a pivot pin 33. With the provision of the arm unit 3, ongoing movement of the lower limb structure 12 relative to the upper limb structure 11 from an extended position (FIGS. 1 and 2) to a flexed position (FIG. 7) about the joint 13 can be regulated.

In an embodiment shown in FIG. 1, the arm unit 3 is provided on the first lateral side 27 (i.e., the outer side of the leg 1).

In an embodiment shown in FIG. 1, the coupled end portion 312 of the upper arm 31 is in a form of an upper lug 304 having an upper front area 313 and an upper rear area 314, and the coupled end portion 312 of the lower arm 31' is in a form of a lower lug 305 having a lower front area 315 and a lower rear area 316. The upper lug 304 and the lower lug 305 define an upper hole 306 and a lower hole 307, respectively.

The strap unit 4 includes a first strap 41 and a second strap 42 which are wound about the web 2 to intersect with each other. Each of the first and second straps 41, 42 is coupled between the coupled end portions 312 of the upper and lower arms 31, 31'.

In an embodiment shown in FIGS. 1 to 3, each of the first and second straps 41, 42 is made of an elastically stretchable material. The first strap 41 has a first upper end 411 coupled to the coupled end portion 312 of the upper arm 31, and a first lower end 412 coupled to the coupled end portion 312 of the lower arm 31'. The second strap 42 has a second upper end 421 coupled to the coupled end portion 312 of the upper arm 31, and a second lower end 422 coupled to the coupled end portion 312 of the lower arm 31'.

In an embodiment shown in FIGS. 1 to 3, the first and second straps 41, 42 are helically wound about the web 2 and intersect with each other to form an intersecting portion 40 for being disposed at a posterior of the joint 13. As shown in FIG. 2, the intersecting portion 40 may be located at the rear side 26 in proximity to the second lateral side 28.

In an embodiment shown in FIG. 1, the first upper end 411 is coupled to the upper front area 313, the first lower end 412 is coupled to the lower rear area 316, the second upper end 421 is coupled to the upper rear area 314, and the second lower end 422 is coupled to the lower front area 315.

The at least one fastening subassembly 5 is configured to permit at least one of the first upper and lower ends 411, 412 and the second upper and lower ends 421, 422 to be turnably coupled to a corresponding one of the coupled end portions 312 of the upper and lower arms 31, 31'.

Figure 4:
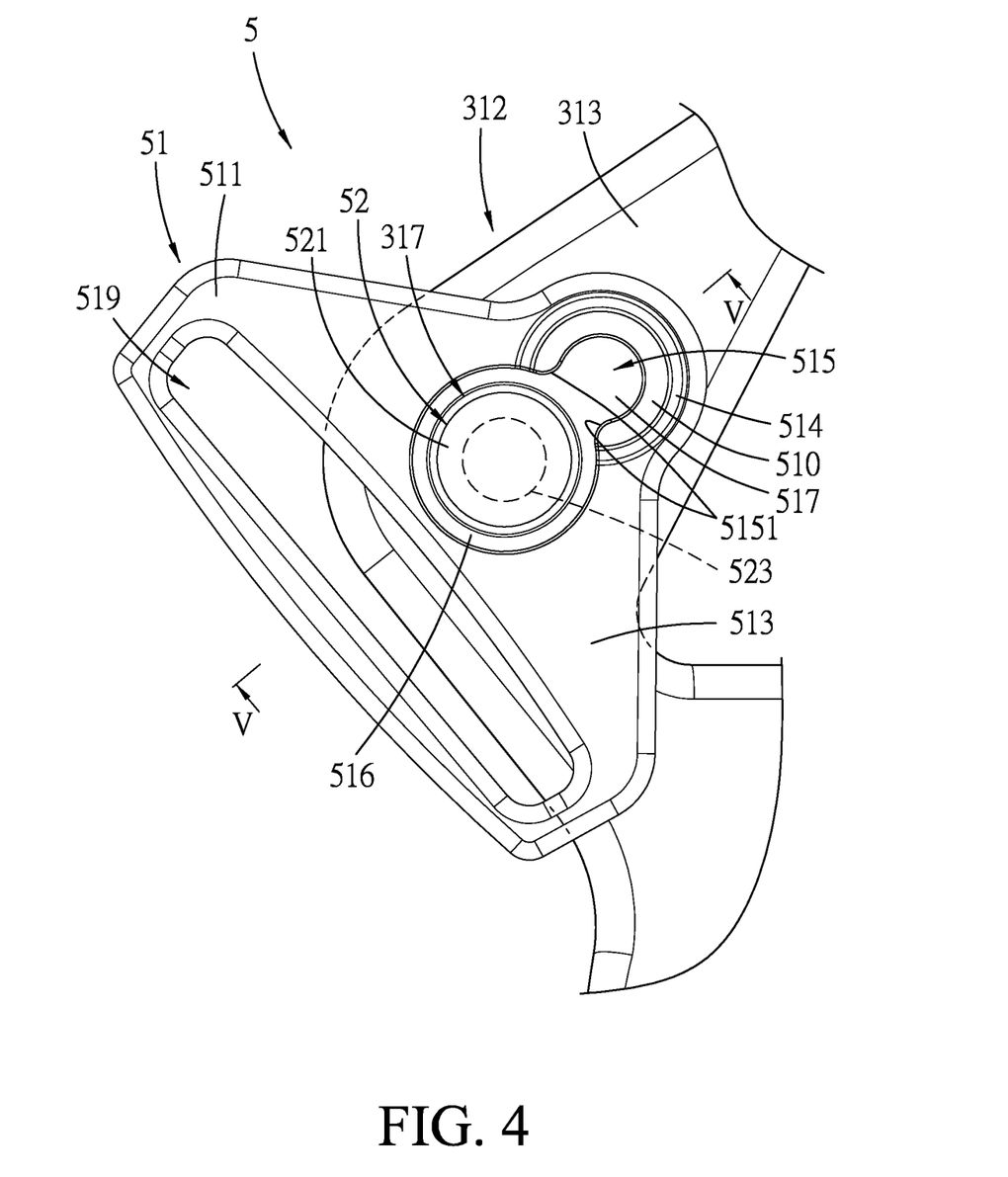
FIG. 4 is a fragmentary enlarged view of the first embodiment illustrating a fastening subassembly.

In an embodiment shown in FIGS. 1, 3, and 4, the at least one fastening subassembly 5 may include an end piece 51 and a clasp member 52. The end piece 51 is coupled to one of the first upper end 411 and the second lower end 422. The clasp member 52 is configured to turnably and fittingly engage the end piece 51 and a corresponding one of the upper front area 313 and the lower front area 315 so as to permit the one of the first upper end 411 and the second lower end 422 to be turnably coupled to the corresponding one of the upper front area 313 and the lower front area 315.

In an embodiment shown in FIGS. 1 and 3, the joint orthosis assembly 200 may include two of the fastening subassemblies 5. The end piece 51 of each of the fastening subassemblies 5 is coupled to a respective one of the first upper end 411 and the second lower end 422. The clasp member 52 of each of the fastening subassemblies 5 is configured to turnably and fittingly engage the end piece 51 and a respective one of the upper front area 313 and the lower front area 315 so as to permit each of the first upper end 411 and the second lower end 422 to be turnably coupled to the respective one of the upper front area 313 and the lower front area 315.

Figure 5:
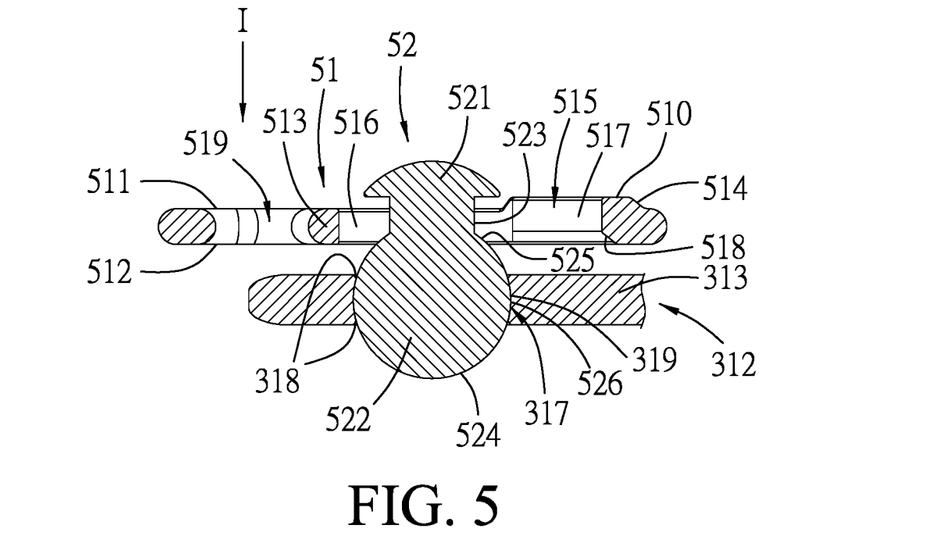
FIG. 5 is a fragmentary cross-sectional view taken along line V-V of FIG. 4.
Figure 6:
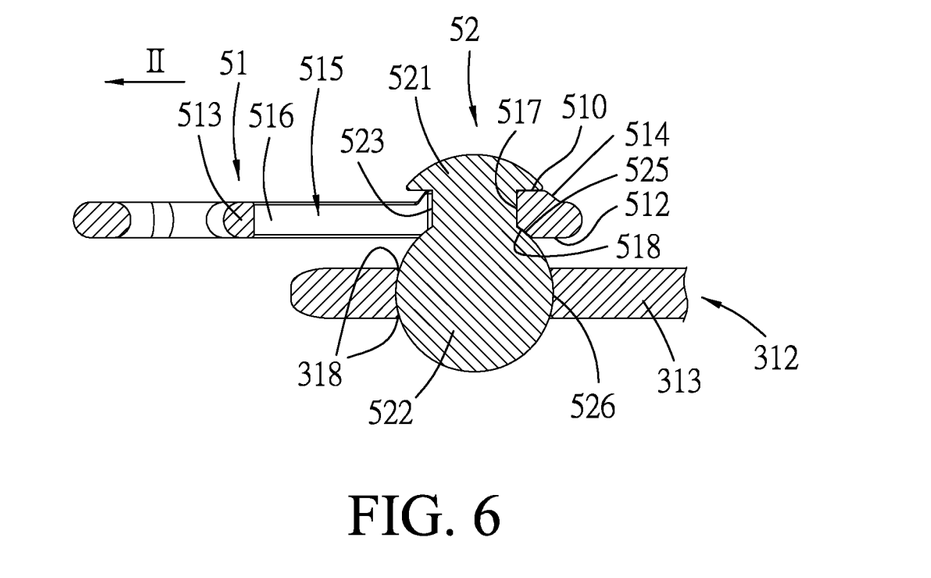
FIG. 6 is similar to FIG. 5 but illustrating a clasp member in turnable and fitting engagement with an end piece in the fastening subassembly.

In an embodiments shown in FIGS. 3 to 6, the end piece 51 of each of the fastening subassemblies 5 has an outward surface 511 and an inward surface 512 for confronting a respective one of the upper front area 313 and the lower front area 315, and includes a proximate portion 513 and a distal portion 514 relative to the respective one of the first upper end 411 and the second lower end 422. The distal portion 514 has a larger thickness than the proximate portion 513 to permit the outward surface 511 to have an elevated region 510 on the distal portion 514. The end piece 51 is formed with a through hole 515 including a guide hole portion 516 and a retaining hole portion 517. The guide hole portion 516 is formed in the proximate portion 513. The retaining hole portion 517 is formed in the distal portion 514 to be in communication with the guide hole portion 516, and has a smaller dimension than the guide hole portion 516. Please note that because the fastening subassemblies 5 have similar configuration, only one of the fastening subassemblies 5 for coupling the first upper end 411 to the upper front area 313 is shown in FIGS. 4 to 6.

Each of the upper front area 313 and the lower front area 315 is formed with a through bore 317 having an inner spherical surface 319. The through bore 317 extends through inner and outer surfaces of a respective one of the upper front area 313 and the lower front area 315 to have two circular openings 318 with the same dimension. Please note that since the through bores 317 of the upper front area 313 and the lower front area 315 have similar configuration, only the through bore 317 formed in the upper front area 313 is shown in FIGS. 4 to 6 for the sake of brevity.

In each of the fastening subassemblies 5, the clasp member 52 is detachably fastened to the end piece 51, and includes an enlarged head 521, a rolling ball portion 522, and a neck portion 523.

The enlarged head 521 has a circular contour with a dimension which is smaller than that of the guide hole portion 516, and which is larger than that of the retaining hole portion 517.

The rolling ball portion 522 has an outer peripheral surface 524 which includes a proximal surface region 525 and a distal surface region 526 relative to the enlarged head 521. The distal surface region 526 is configured to be rollably retained by the inner spherical surface 319 of the through bore 317 of a respective one of the upper front area 313 and the lower front area 315 so as to prevent the rolling ball portion 522 from being disengaged from the respective through bore 317. Therefore, the clasp member 52 of each of the fastening subassemblies 5 is allowed to turnably and fittingly engage a respective one of the upper front area 313 and the lower front area 315. Please note that in this embodiment, the connection between the clasp member 52 and the respective one of the upper front area 313 and the lower front area 315 is a universal joint.

The neck portion 523 is disposed between the enlarged head 521 and the rolling ball portion 522, and is configured to be in a cylindrical form. An outer dimension of the neck portion 523 is smaller than those of the enlarged head 521 and the rolling ball portion 522. When the enlarged head 521 is brought to extend through the guide hole portion 516 to place the neck portion 523 in the guide hole portion 516, the neck portion 523 is permitted to be forced into and fittingly retained in the retaining hole portion 517 to cause the enlarged head 521 and the proximal surface region 525 to respectively and slidably engage the elevated region 510 and the inward surface 512 of the end piece 51, thereby allowing the clasp member 52 to turnably and fittingly engage the end piece 51.

In an embodiment shown in FIG. 4, the end piece 51 has two protuberances 5151 which are provided between the guide hole portion 516 and the retaining hole portion 517 and which define therebetween a gap slightly smaller than the outer dimension of the neck portion 523. Once the neck portion 523 is forced through the gap between the protuberances 5151 to be fittingly retained in the retaining hole portion 517, the neck portion 523 may be prevented from undesirably disengaged from the retaining hole portion 517.

In an embodiment shown in FIGS. 5 and 6, the inward surface 512 of the end piece 51 has a rounded contact area 518 which extends around the retaining hole portion 517, and which is configured to be in rolling contact with the proximal surface region 525 when the neck portion 523 is fittingly retained in the retaining hole portion 517. Therefore, the clasp member 52 may have an increased contact surface area with the end piece 51 and may be further stabilized and be prevented from wobbling.

In an embodiment shown in FIGS. 1, 3, and 4, each of the first upper and lower ends 411, 412 and the second upper and lower ends 421, 422 is in a form of a loop. The loops of the first lower end 412 and the second upper end 421 are respectively secured to the lower rear area 316 and the upper rear area 314. The proximate portion 513 of the end piece 51 has an elongated slot 519. The loops of the first upper end 411 and the second lower end 422 are engaged in the elongated slots 519 of the end pieces 51 of the fastening subassemblies 5, respectively.

In an embodiment shown in FIG. 1, the joint orthosis assembly 200 may further include a retaining unit 6 which includes an upper retaining patch 61 and a lower retaining patch 62. The upper retaining patch 61 is configured to couple and retain the upper lug 304 on the upper web portion 201. The lower retaining patch 62 is configured to couple and retain the lower lug 305 on the lower web portion 202. For example, each of the upper retaining patches 61, 62 may cover a respective one of the upper and lower lugs 304, 305 and have two ends thereof being stitched to a respective one of the upper and lower web portions 201, 202.

In an embodiment shown in FIG. 1, the retaining unit 6 further includes a middle retaining patch 63 which has two patch ends 631 secured respectively to the upper and lower web portions 201, 202 through the upper and lower holes 306, 307 so as to permit the upper and lower arms 31, 31' to be partially retained in a space 60 between the web 2 and the middle retaining patch 63. As shown in FIG. 1, the upper and lower lugs 304, 305 may be exposed from the middle retaining patch 63. The middle retaining patch 63 may be secured to the web 2 by, for example, stitching. Each of the upper, lower, and middle retaining patches 61, 62, 63 may be made of an elastically stretchable material.

To wear the joint orthosis assembly 200 on the leg 1, the web 2 as shown in FIG. 3 is disposed at a posterior side of the leg 1. Then, the first marginal region 215 is bent forwardly and the second marginal region 216 is bent forwardly to cover and to be fastened to the first marginal region 214 by means of the fastening engagement between the first and second fastening strips 23, 24, thereby tightly wrapping the web 2 on the leg 1.

Thereafter, the first strap 41 secured to the lower rear area 316 at the first lateral side 27 of the wrapped web 2 is wound upwardly about the wrapped web 2 to pass over the rear side 26, the second lateral side 28, and the front side 25, and then the end piece 51 coupled on the first upper end 411 of the first strap 41 is brought into fastening engagement with the clasp member 52 on the upper front area 313 at the first lateral side 27, thereby tightly positioning the first strap 41 on the wrapped web 2. The second strap 42 secured to the upper rear area 314 at the first lateral side 27 of the wrapped web 2 is wound downwardly about the wrapped web 2 to pass over the first strap 41 at the rear side 26, the second lateral side 28, and the front side 25, and then the end piece 51 coupled on the second lower end 422 of the second strap 42 is brought into fastening engagement with the clasp member 52 on the lower front area 315 at the first lateral side 27, thereby tightly positioning the second strap 42 on the wrapped web 2.

When fastening the end piece 51 to the clasp member 52, the end piece 51 is moved along an arrow (I) shown in FIG. 5 to permit the enlarged head 521 to extend through the guide hole portion 516 to place the neck portion 523 in the guide hole portion 516. Then, as the end piece 51 is moved along an arrow (II) shown in FIG. 6, the protuberances 5151 are deformed by the neck portion 523 to permit the neck portion 523 to be forced into the retaining hole portion 517. Afterwards, the protuberances 5151 return to the original forms and the neck portion 523 is fittingly retained in the retaining hole portion 517. At the same time, the enlarged head 521 and the proximal surface region 525 are respectively brought into slidably engagement with the elevated region 510 and the rounded contact area 518 of the end piece 51. In view of the provision of the elevated region 510 on the outward surface 511, a user may be less likely to try to erroneously couple the end piece 51 to the clasp member 51 with the outward surface 511 of the end piece 51 confronting the upper front area 313 or the lower front area 315.

Figure 8:
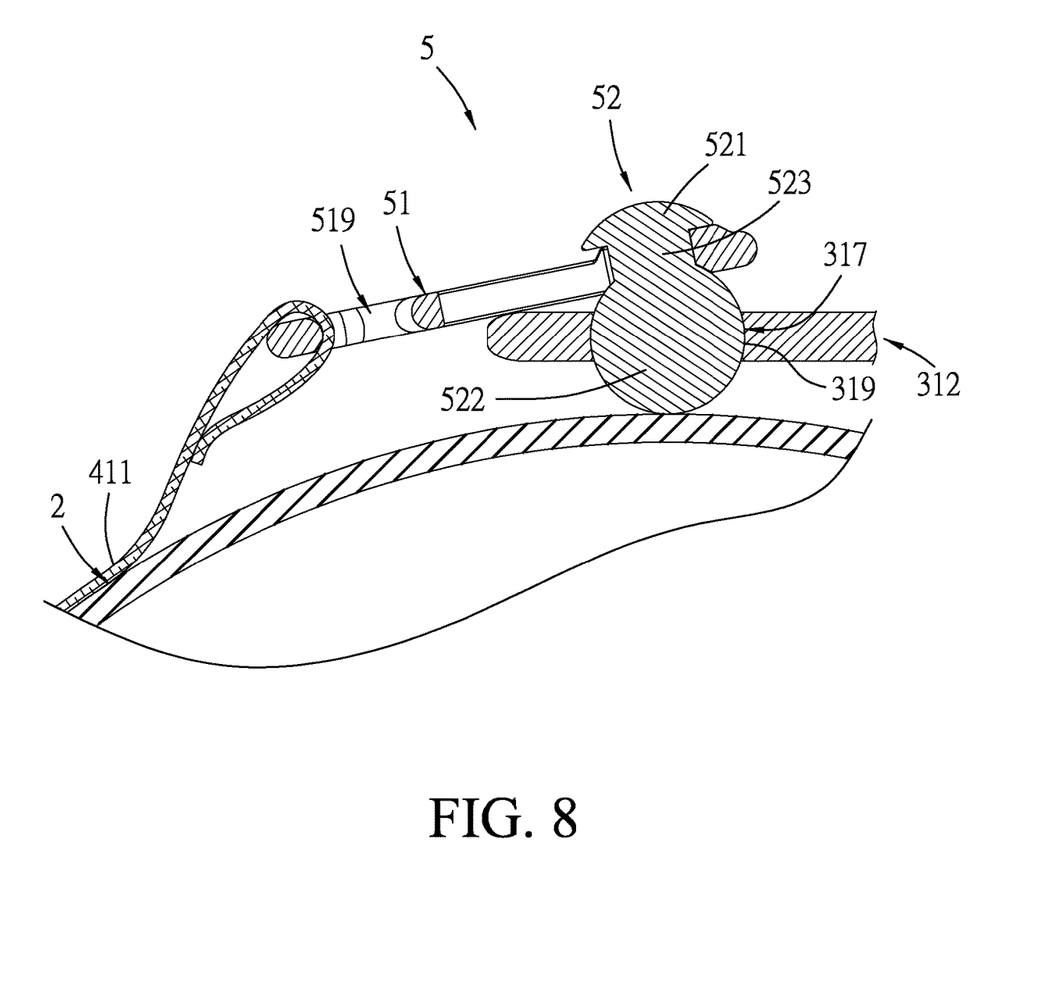
FIG. 8 is a fragmentary cross-sectional view of the first embodiment illustrating a state of the fastening subassembly when the leg is in the flexed position.

During ongoing movement of the calf limb 12 relative to the thigh limb 11 between the extended position (FIGS. 1 and 2) and the flexed position (FIGS. 7 and 8) about the knee joint 13, the web 2 and the arm unit 3 are bent with the leg 1, and the first and second straps 41, 42 may slide on the web 2. Because the end piece 51 of each of the fastening subassemblies 5 is turnable relative to a corresponding one of the upper front area 313 and the lower front area 315 along an arrow (R1) shown in FIG. 7 or an arrow (R2) shown in FIG. 1, the first and second straps 41, 42 may always have a relatively large contact area with the web 2 (i.e., the first and second straps 41, 42 may be always fittingly tightened on the web 2).

In addition, because the web 2 and the first and second straps 41, 42 are elastically stretchable, the beneficial function of the joint orthosis assembly 200 may not be adversely affected even if the web 2 is wrapped on a leg 1 with a different dimension.

Figure 9:
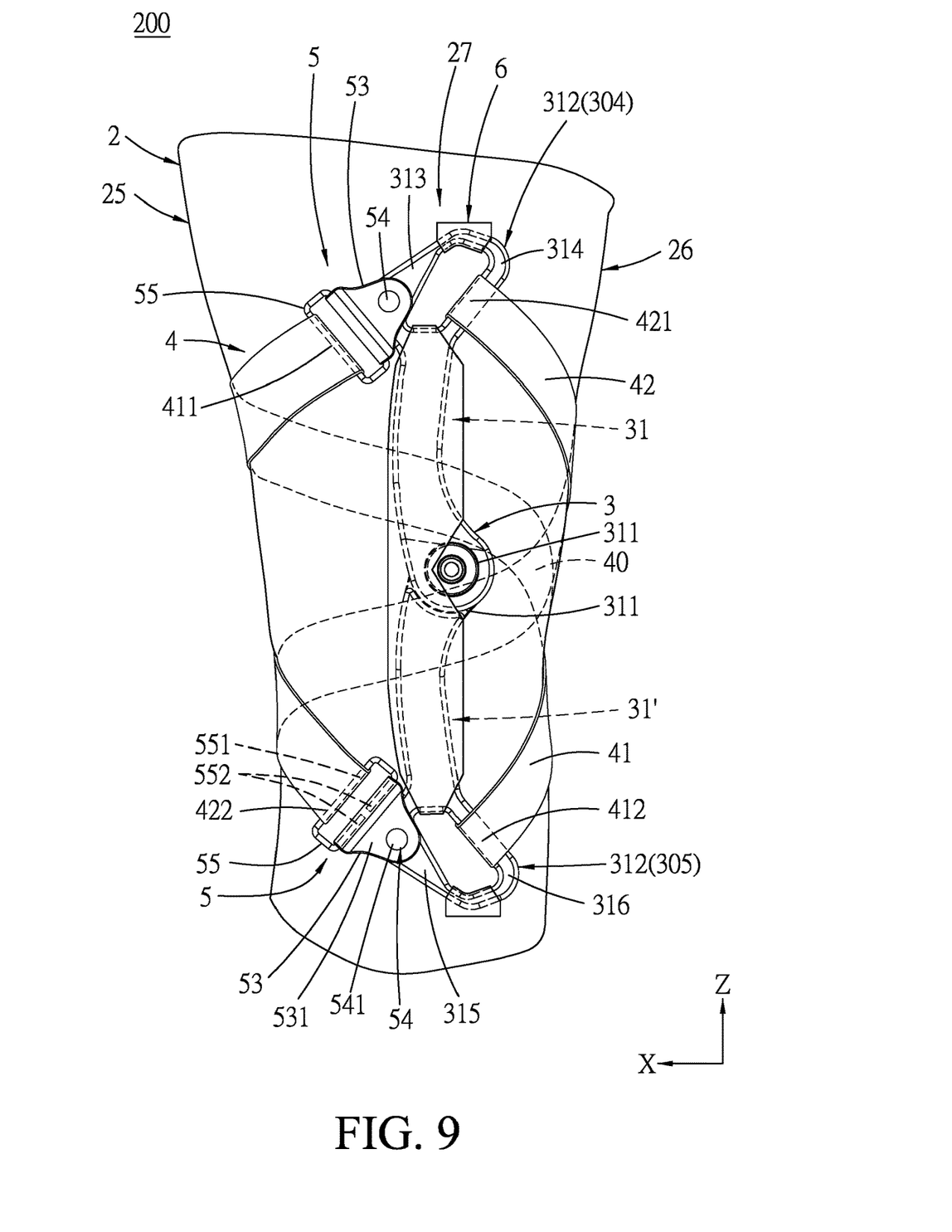
FIG. 9 is a side view of a joint orthosis assembly according to a second embodiment of the disclosure.
Figure 10:
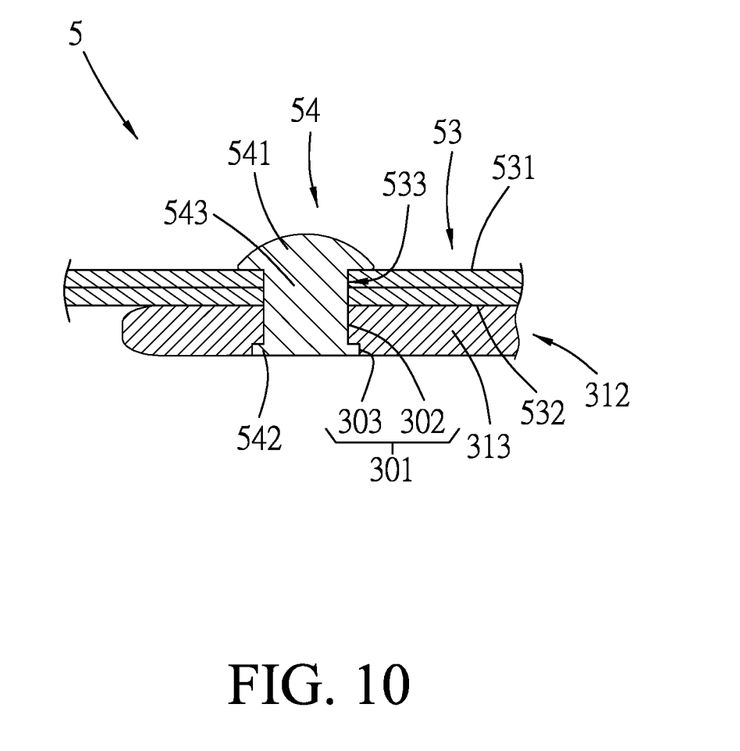
FIG. 10 is a fragmentary cross-sectional view of the second embodiment illustrating a fastening subassembly.

FIGS. 9 and 10 illustrate a joint orthosis assembly 200 according to a second embodiment of the disclosure. The second embodiment is similar to the first embodiment except that in the second embodiment, the web 2 extends circumferentially to be in a sleeve form. Therefore, the joint orthosis assembly 200 may be worn on the leg 1 by sleeving the web 2 on the leg 1.

In addition, each of the fastening subassemblies 5 includes an end piece 53 and a clasp member 54. The end piece 53 of each of the fastening subassemblies 5 is coupled to a respective one of the first upper end 411 and the second lower end 422. The clasp member 54 of each of the fastening subassemblies 5 is configured to turnably and fittingly engage the end piece 53 and a respective one of the upper front area 313 and the lower front area 315 so as to permit each of the first upper end 411 and the second lower end 422 to be turnably coupled to the respective one of the upper front area 313 and the lower front area 315.

In an embodiment shown in FIGS. 9 and 10, the end piece 53 of each of the fastening subassemblies 5 has an outward surface 531 and an inward surface 532 for confronting a respective one of the upper front area 313 and the lower front area 315, and is formed with a first retaining hole 533. Please note that because the fastening subassemblies 5 have similar configuration, only one of the fastening subassemblies 5 for coupling the first upper end 411 to the upper front area 313 is shown in FIG. 10.

Each of the upper front area 313 and the lower front area 315 is formed with a second retaining hole 301 which includes an outer hole portion 302 and an inner hole portion 303 having a larger dimension than the outer hole portion 302. Please note that since the second retaining holes 301 of the upper front area 313 and the lower front area 315 have similar configuration, only the second retaining hole 301 formed in the upper front area 313 is shown in FIG. 10 for the sake of brevity.

The clasp member 54 of each of the fastening subassemblies 5 includes an enlarged head 541, a flange end 542, and a neck portion 543. The enlarged head 541 has a larger dimension than the first retaining hole 533. The flange end 542 is configured to be turnably and fittingly retained in the inner hole portion 303 of the second retaining hole 301 of a respective one of the upper front area 313 and the lower front area 315. The neck portion 543 interconnects the enlarged head 541 and the flange end 543 and is configured to be turnably and fittingly retained in the first retaining hole 533 and the outer hole portion 302 of the second retaining hole 301 of a respective one of the upper front area 313 and the lower front area 315 so as to permit the enlarged head 541 to be turnably engaged on the outward surface 531 of the end piece 53, thereby allowing the clasp member 54 of each of the fastening subassemblies 5 to turnably and fittingly engage the end piece 53 and the respective one of the upper front area 313 and the lower front area 315.

In an embodiment shown in FIG. 9, each of the fastening subassemblies 5 may further include a hook piece 55 having an elongated portion 551 and two bent end portions 552 which extend respectively from two ends of the elongated portion 551, and which are bent toward each other. The end piece 53 is folded to grip the bent end portions 552 of the hook piece 55. The loops of the first upper end 411 and the second lower end 422 are respectively secured to the elongated portions 551 of the hook pieces 55 of the fastening subassemblies 5.

Figure 11:
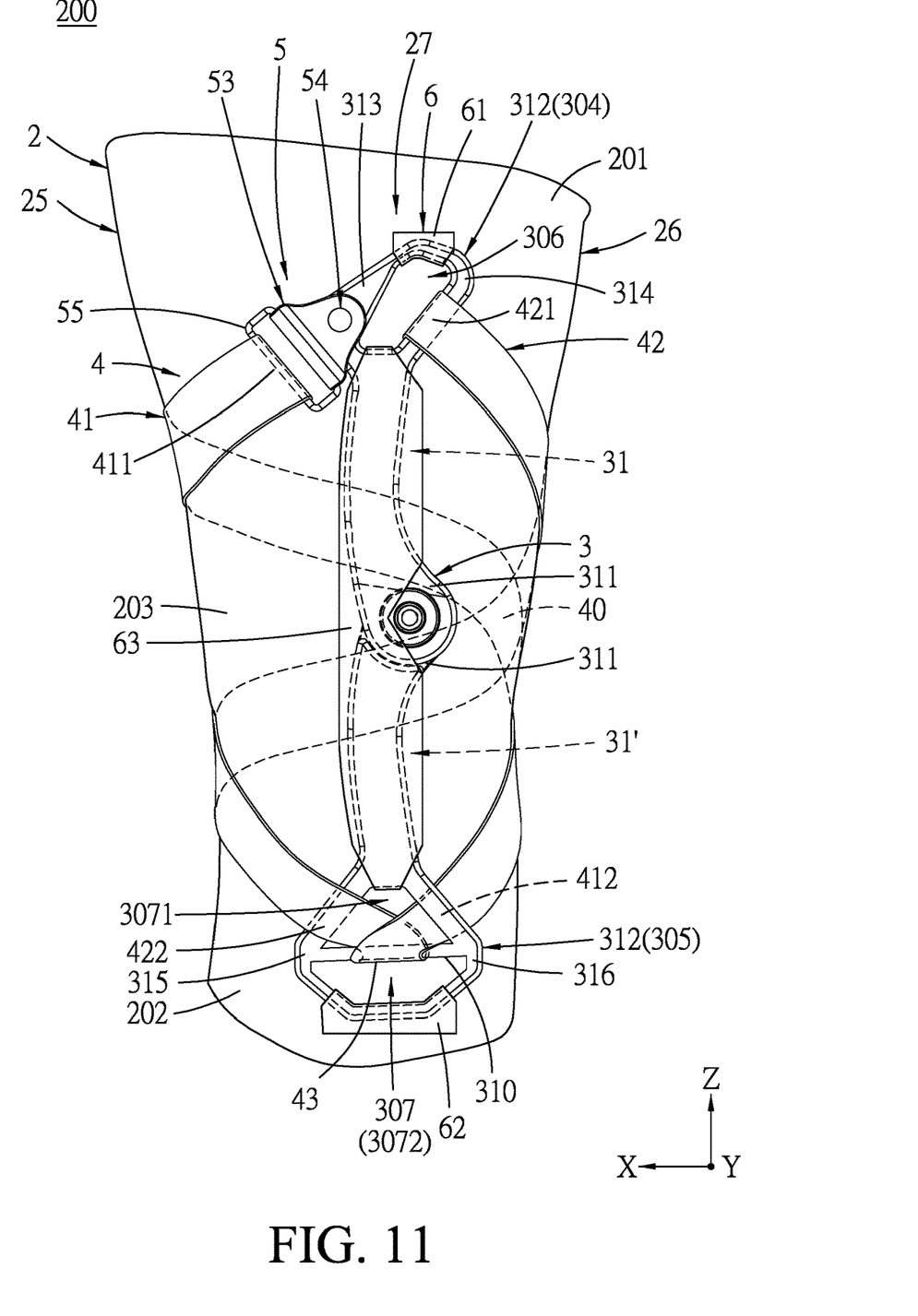
FIG. 11 is a side view of a joint orthosis assembly according to a third embodiment of the disclosure.
Figure 12:
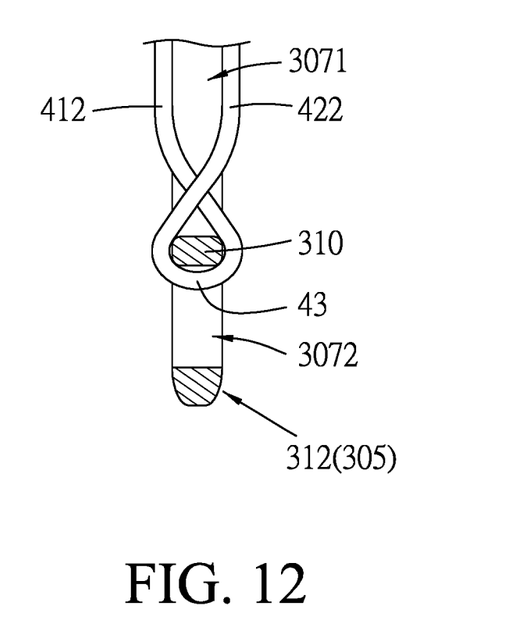
FIG. 12 is a fragmentary partially cross-sectional view of the third embodiment illustrating an interconnecting strap, which interconnects first and second straps, and which winds around a bridge piece.

FIGS. 11 and 12 illustrate a joint orthosis assembly 200 according to a third embodiment of the disclosure. The third embodiment is similar to the second embodiment except that in the third embodiment, the joint orthosis assembly 200 includes a single fastening subassembly 5. The end piece 53 is coupled to first upper end 411 through the hook piece 55, and the clasp member 54 is configured to turnably and fittingly engage the end piece 53 and the upper front area 313 so as to permit the first upper end 411 to be turnably coupled to the upper front area 313.

In an embodiment shown in FIGS. 11 and 12, the lower lug 305 may include a bridge piece 310 which interconnects the lower front area 315 and the lower rear area 316 in the lower hole 307 to partition the lower hole 307 into a first hole portion 3071 and a second hole portion 3072.

Furthermore, the strap unit 4 may further include an interconnecting strap 43 which extends from the first lower end 412 of the first strap 41 to the second lower end 422 of the second strap 42 and which winds around the bridge piece 310, so as to permit the first lower end 412 and the second lower end 422 to be respectively coupled to the lower rear area 316 and the lower front area 315. The interconnecting strap 43 may be made of an elastically stretchable material.

In an embodiment shown in FIGS. 11 and 12, the first lower end 412 is engaged between the web 2 and the lower rear area 316, and the second lower end 422 is engaged on an outer surface of the lower front area 315. The interconnecting strap 43 extends from the first lower end 412 through the first hole portion 3071 to move outwardly, winds around the bridge piece 310 by extending through the second hole portion 3072 to move inwardly and further extending through the first hole portion 3071 to move outwardly, and is connected to the second lower end 422.

In an embodiment shown in FIGS. 11 and 12, the first strap 41, the second strap 42, and the interconnecting strap 43 are integrally formed as a continuous strap.

Alternatively, in other not-shown embodiments, the end piece 53 is coupled to the second lower end 422, and the clasp member 54 is configured to turnably and fittingly engage the end piece 53 and the lower front area 315 so as to permit the second lower end 422 to be turnably coupled to the lower front area 315. The bridge piece 310 is formed to interconnect the upper front area 313 and the upper rear area 314. The interconnecting strap 43 extends from the first upper end 411 of the first strap 41 to the second upper end 421 of the second strap 42 and winds around the bridge piece 310.

With the provision of the joint orthosis assembly 200, during ongoing movement of the calf limb 12 relative to the thigh limb 11 between the extended position (FIGS. 1 and 2) and the flexed position (FIG. 7) about the knee joint 13, while the web 2 and the arm unit 3 are bent with the leg 1, the first and second straps 41, 42 may be always fittingly tightened on the web 2.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A joint orthosis assembly for stabilizing a joint between an upper limb structure and a lower limb structure, said joint orthosis assembly comprising:
 a web having an upper web portion for being wrapped on the upper limb structure, a lower web portion for being wrapped on the lower limb structure, and a middle web portion disposed between said upper and lower web portions for being wrapped around the joint, said web defining a front side, a rear side opposite to said front side in a front-rear direction, a first lateral side, and a second lateral side opposite to said first lateral side in a left-right direction;
 an arm unit provided on said first lateral side of said web, and including an upper arm for being disposed at the upper limb structure, and a lower arm for being disposed at the lower limb structure, each of said upper and lower arms including a pivot end portion and a coupled end portion which is coupled to be retained on a respective one of said upper and lower web portions, said pivot end portions of said upper and lower arms being at least partially overlapped to form an overlapped zone and being pivotally connected to each other on said middle web portion by a pivot pin that extends through said overlapped zone, said coupled end portion of said upper arm being in a form of an upper lug which has an upper front area and an upper rear area and which defines an upper hole, said coupled end portion of said lower arm being in a form of a lower lug which has a lower front area and a lower rear area and which defines a lower hole;
 a strap unit including a first strap and a second strap which are wound about said web to intersect with each other, said first strap having a first upper end coupled to said upper front area of said upper lug, and a first lower end extending into said lower hole to be coupled to said lower rear area of said lower lug, said second strap having a second upper end extending into said upper hole to be coupled to said upper rear area of said upper lug, and a second lower end coupled to said lower front area of said lower lug; and
 at least one fastening subassembly configured to permit at least one of said first upper end and said second lower end to be turnably coupled to a corresponding one of said upper front area and said lower front area;
 wherein said first and second straps are helically wound about said web and intersect with each other to form an intersecting portion for being disposed at a posterior of the joint;
 wherein the corresponding one of said upper front area and said lower front area is formed with a through bore having an inner spherical surface, said through bore extending through inner and outer surfaces of the corresponding one of said upper front area and said lower front area to have two circular openings with same dimension;
 wherein said at least one fastening subassembly includes an end piece coupled to said at least one of said first upper end and said second lower end, and
 a clasp member configured to turnably and fittingly engage said end piece and the corresponding one of said upper front area and said lower front area so as to permit said at least one of said first upper end and said second lower end to be turnably coupled to the corresponding one of said upper front area and said lower front area;
 wherein said clasp member is detachably fastened to said end piece, and includes
 an enlarged head,
 a rolling ball portion having an outer peripheral surface which includes a proximal surface region and a distal surface region relative to said enlarged head, said distal surface region being configured to be rollably retained by said inner spherical surface of said through bore of the corresponding one of said upper front area and said lower front area, thereby allowing said clasp member of the at least one of said fastening subassemblies to turnably and fittingly engage the corresponding one of said upper front area and said lower front area and maintain engagement as the upper limb structure and lower limb structure bend at the joint, and a neck portion which is disposed between said enlarged head and said rolling ball portion; and wherein said rolling ball portion extends through said through bore, and has two regions which protrude outwardly of said two circular openings of said through bore, respectively.

2. The joint orthosis assembly according to claim 1, further comprising a retaining unit which includes an upper retaining patch configured to couple and retain said upper lug on said upper web portion, and a lower retaining patch configured to couple and retain said lower lug on said lower web portion.

3. The joint orthosis assembly according to claim 2, wherein said retaining unit further includes a middle retaining patch which has two patch ends secured respectively to said upper and lower web portions through said upper and lower holes so as to permit said upper and lower arms to be partially retained in a space between said web and said middle retaining patch.

4. The joint orthosis assembly according to claim 1, wherein said web is made of an elastically stretchable material.

5. The joint orthosis assembly according to claim 1, wherein each of said first and second straps is made of an elastically stretchable material.

6. The joint orthosis assembly according to claim 1, which comprises two of said fastening subassemblies, wherein said end piece of each of said fastening subassemblies is coupled to a respective one of said first upper end and said second lower end;

wherein said clasp member of each of said fastening subassemblies is configured to turnably and fittingly engage said end piece and a respective one of said upper front area and said lower front area so as to permit each of said first upper end and said second lower end to be turnably coupled to the respective one of said upper front area and said lower front area;

wherein each of said upper front area and said lower front area is formed with said through bore; and wherein in each of said fastening subassemblies, said distal surface region of said rolling ball portion is configured to be rollably retained by said inner spherical surface of said through bore of the respective one of said upper front area and said lower front area.

7. The joint orthosis assembly according to claim 6, wherein said web extends circumferentially to terminate at a first marginal region and a second marginal region which are configured to be detachably fastened to each other so as to form an opening for exposing an anterior of the joint.

8. The joint orthosis assembly according to claim 7, wherein said end piece of each of said fastening subassemblies has an outward surface and an inward surface for confronting a respective one of said upper front area and said lower front area, and includes a proximate portion and a distal portion relative to the respective one of said first upper end and said second lower end, said distal portion having a larger thickness than said proximate portion to permit said outward surface to have an elevated region on said distal portion, said end piece being formed with a through hole including a guide hole portion which is formed in said proximate portion, and a retaining hole portion which is formed in said distal portion to be in communication with said guide hole portion, and which has a smaller dimension than said guide hole portion;

wherein said enlarged head has a dimension which is smaller than that of said guide hole portion, and which is larger than that of said retaining hole portion; and wherein said neck portion is configured such that when said enlarged head is brought to extend through said guide hole portion to place said neck portion in said guide hole portion, said neck portion is permitted to be forced into and fittingly retained in said retaining hole portion to cause said enlarged head and said proximal surface region to respectively and slidably engage said elevated region and said inward surface of said end piece, thereby allowing said clasp member to turnably and fittingly engage said end piece.

9. The joint orthosis assembly according to claim 8, wherein said inward surface of said end piece has a rounded contact area which extends around said retaining hole portion, and which is configured to be in rolling contact with said proximal surface region when said neck portion is fittingly retained in said retaining hole portion.

10. The joint orthosis assembly according to claim 6, wherein said web extends circumferentially to be in a sleeve form.

11. The joint orthosis assembly according to claim 1, wherein said end piece is coupled to said first upper end, and said clasp member is configured to turnably and fittingly engage said end piece and said upper front area so as to permit said first upper end to be turnably coupled to said upper front area.

12. The joint orthosis assembly according to claim 11, wherein said lower lug defines a lower hole and includes a bridge piece which interconnects said lower front area and said lower rear area in said lower hole; and wherein said strap unit further includes an interconnecting strap which extends from said first lower end of said first strap to said second lower end of said second strap, and which winds around said bridge piece, so as to permit said first lower end and said second lower end to be respectively coupled to said lower rear area and said lower front area.

13. The joint orthosis assembly according to claim 12, wherein said first strap, said second strap, and said interconnecting strap are integrally formed as a continuous strap.

* * * * *